(12) United States Patent
Schers et al.

(10) Patent No.: US 8,771,188 B2
(45) Date of Patent: Jul. 8, 2014

(54) ULTRASONIC BONE MOTION TRACKING SYSTEM

(75) Inventors: Jonathan Schers, Grenoble (FR); Christopher Plaskos, New York, NY (US); Stephane Lavallee, Saint Martin d'Uriage (FR); Jocelyne Troccaz, Eybens (FR)

(73) Assignee: Perception Raisonnement Action en Medecine, La Tronche (FR)

( * ) Notice: Subject to any disclaimer, the term of this patent is extended or adjusted under 35 U.S.C. 154(b) by 834 days.

(21) Appl. No.: 12/143,225

(22) Filed: Jun. 20, 2008

(65) Prior Publication Data

US 2009/0018445 A1 Jan. 15, 2009

Related U.S. Application Data

(60) Provisional application No. 60/945,249, filed on Jun. 20, 2007.

(51) Int. Cl.
*A61B 8/14* (2006.01)

(52) U.S. Cl.
USPC ............ 600/437; 600/439; 600/595; 606/130

(58) Field of Classification Search
None
See application file for complete search history.

(56) References Cited

U.S. PATENT DOCUMENTS

| | | | | |
|---|---|---|---|---|
| 6,048,312 | A * | 4/2000 | Ishrak et al. ................... | 600/443 |
| 2005/0033173 | A1 | 2/2005 | von Behren et al. | |
| 2006/0241447 | A1* | 10/2006 | Harada et al. ................... | 600/443 |
| 2008/0021309 | A1 | 1/2008 | Amiot et al. | |

OTHER PUBLICATIONS

Gobbi et al., Interactive Intra-operative 3D Ultrasound Reconstruction and Visualization, MICCAI '02 Proceedings of the 5th International Conference on Medical Image Computing and Computer-Assisted Intervention-Part II, pp. 156-163, 2002.*
Kryvanos, Computer assisted surgery for fracture reduction and deformity correction of the pelvis and long bones. PhD thesis, University of Mannheim, Germany, 2002.*
Shekhar et al, Mutual Information-Based Rigid and Nonrigid Registration of Ultrasound Volumes, IEEE Transactions on Medical Imaging, vol. 21, No. 1, pp. 9-22, Jan. 2002.
Komistek et al., In Vivo Fluoroscopic Analysis of the Normal Human Knee, Clinical Orthopaedics and Related Research, No. 410, pp. 69-81, 2003.
Chen et al., A system for ultrasound-guided computer-assisted orthopaedic surgery, Computer Aided Surgery, pp. 281-292, Sep. 2005.
Daanen et al., An Information Fusion Method for the Automatic Delineation of the Bone-Soft Tissues Interface in Ultrasound Images, CVAMIA-MMBIA, pp. 218-229, 2004.
Daanen et al., A Fully Automated Method for the Delineation of Osseous Interface in Ultrasound Images, MICCAI, pp. 549-557, 2004.

* cited by examiner

*Primary Examiner* — Long V. Le
*Assistant Examiner* — Farshad Negarestan
(74) *Attorney, Agent, or Firm* — Kim Winston LLP

(57) ABSTRACT

A computerized bone motion tracking system according to one exemplary embodiment is configured to: provide a non-invasive means for accurate measurement and tracking of the motion of a bone using a volumetric ultrasound transducer and a three dimensional position measurement system; provide relative measurements of one bone relative to another bone of a joint; decompose relative joint motion into specific components; and measure joint instability and range of motion.

21 Claims, 6 Drawing Sheets

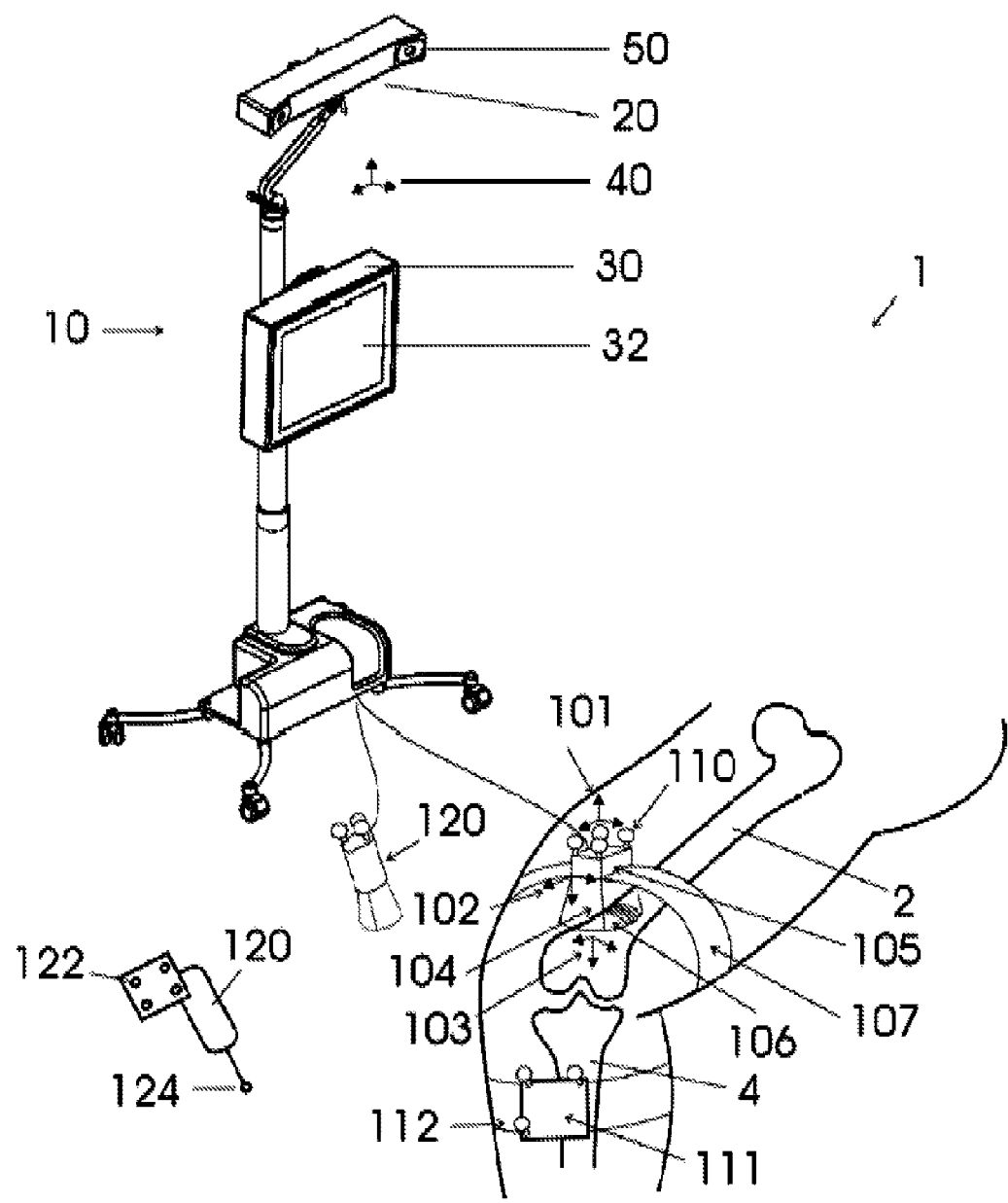

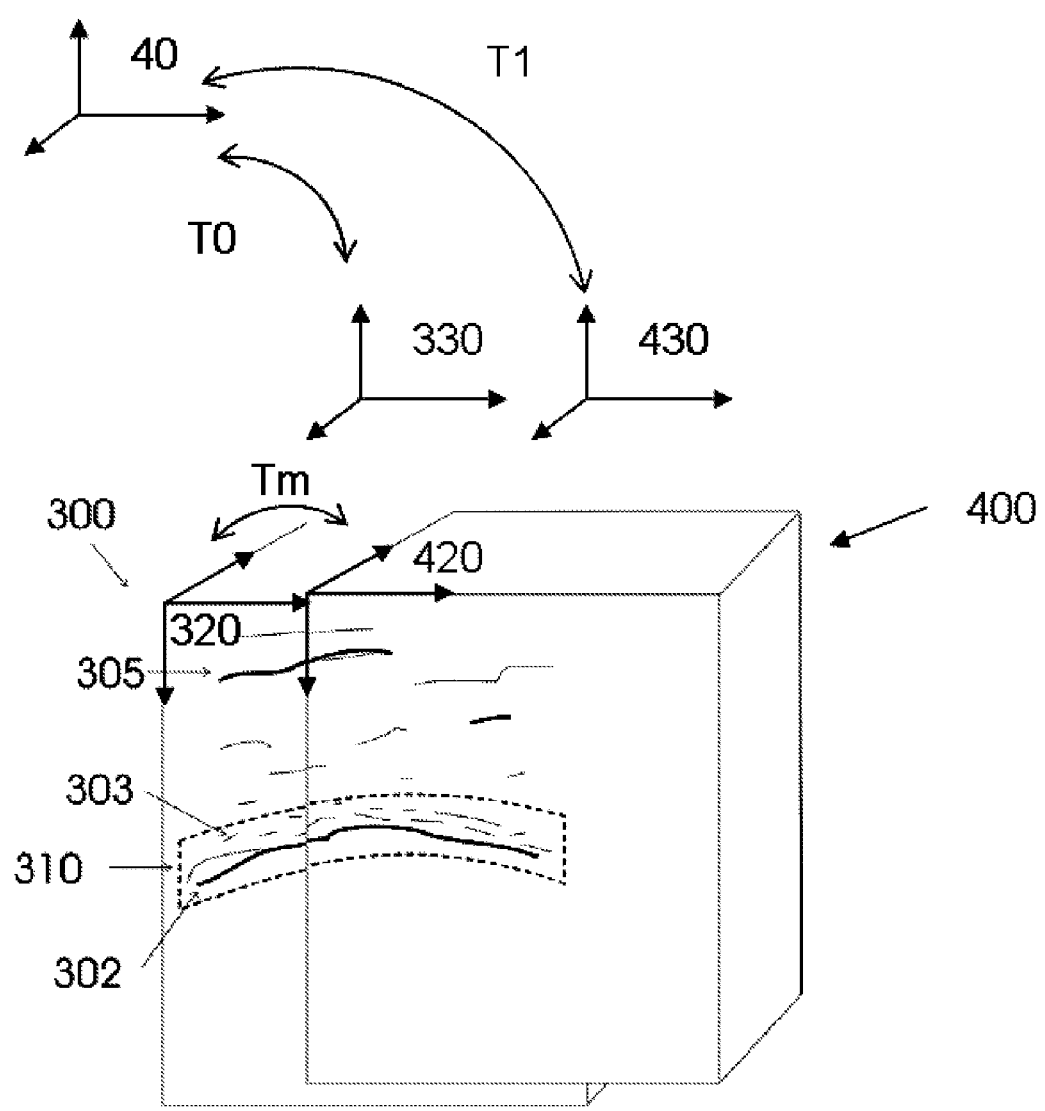

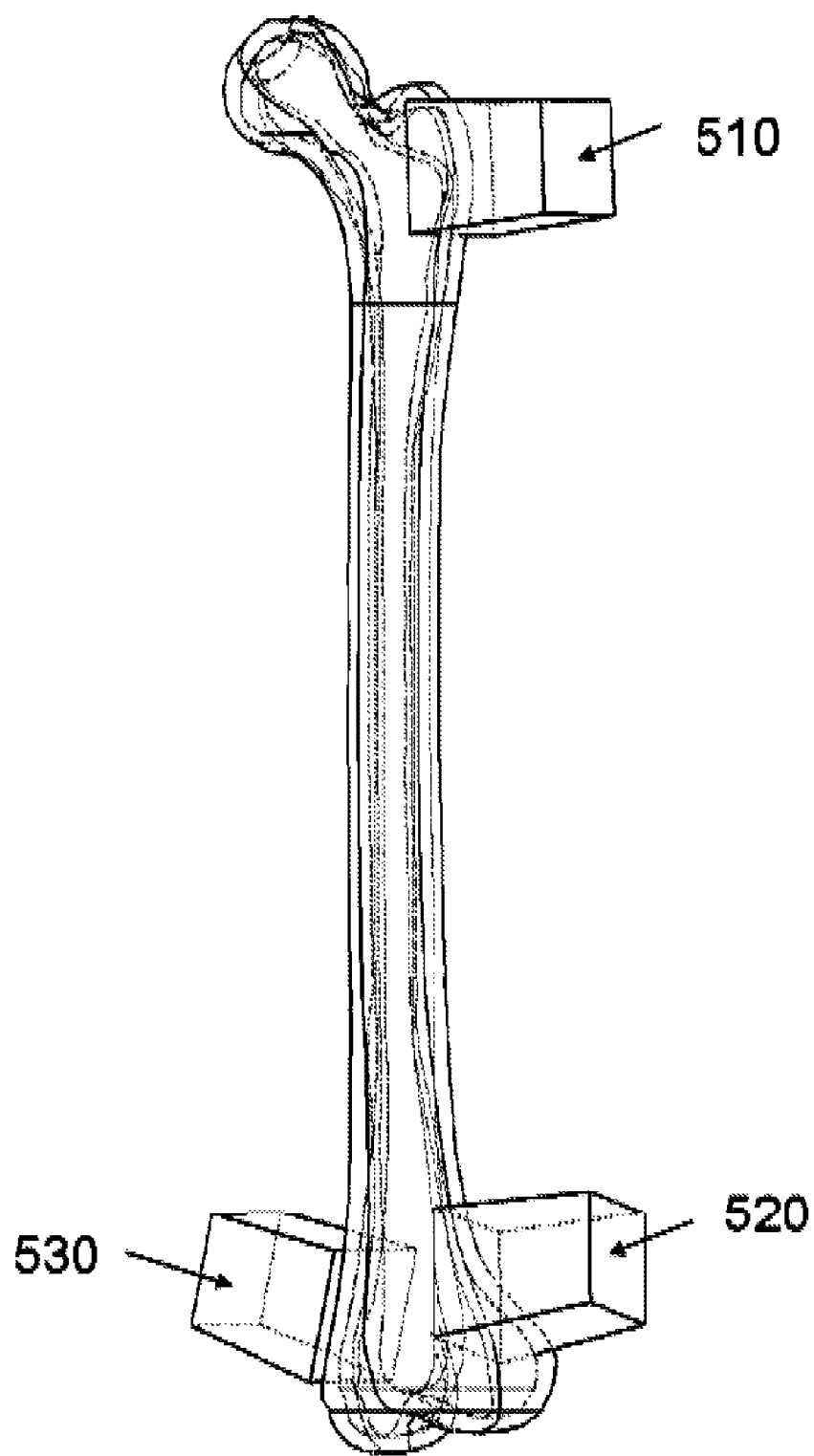

ULTRASONIC BONE MOTION TRACKING SYSTEM

CROSS-REFERENCE TO RELATED APPLICATION

This application claims the benefit of U.S. patent application Ser. No. 60/945,249, filed Jun. 20, 2007, which is hereby incorporated by reference in its entirety.

TECHNICAL FIELD

The present invention relates to the field of computer-assisted surgery and human movement analysis and in particular, to the non-invasive tracking of bone structures.

BACKGROUND

In the field of computer assisted surgery, it is often required to track a structure in a human body, such as a bone or an organ. In particular, in computer assisted orthopaedic surgery, the motion of bones is tracked with a three-dimensional (3D) position measurement system. This is typically carried out by attaching a marker to the bone invasively, by drilling pins or screws into the bone, creating holes and causing trauma to the tissue and structure. This can increase the risk of bone fracture, infection, and cause pain to the patient. Some examples of these intra-operative motion tracking systems can are described in U.S. Patent Application publication No. 20060250300 entitled 'RF system for tracking objects' and in U.S. Patent Application Publication No. 20050245821 entitled "Position Sensing System for Orthopedic Applications", each of which is hereby incorporated by reference in its entirety.

Furthermore, such systems are not suitable for measuring the motion of a subject or patient outside of the operating room, when the patient is not under anesthesia. This is due to the invasiveness of current tracking systems, and the above-mentioned factors. Normally, in the analysis of human movement, such as in gait analysis, the motion of the underlying bones is inferred by tracking the motion of the overlying skin. This is typically carried out by attaching markers to the skin using adhesive means, or straps, or by attaching markers to fitted clothes on the subject. While not invasive, this method has the disadvantage of being less accurate, because of the motion of the skin and other overlying soft-tissues such as muscle with respect to the bone surface.

Other methods for measuring in-vivo bone kinematics use live 2D projected fluoroscopy images and intensity-based three-dimensional to two-dimensional image registration techniques (see for example the article by Komistek et. al. entitled In Vivo Fluoroscopic Analysis of the Normal Human Knee, in CLINICAL ORTHOPAEDICS AND RELATED RESEARCH, Number 410, pp. 69-81, 2003). Komistek's method requires the construction of three-dimensional computer-aided design models from pre-operative segmented computed tomography (CT) or magnetic resonance imaging (MRI) scans, and to register these models to 2D fluoroscopic images using an optimization algorithm that automatically adjusts the pose of the model at various knee flexion angles to best match the anatomy on the projected live images. Disadvantages of such techniques are that large and expensive imaging apparatuses are required, and that they expose the patent to ionizing radiation. Moreover, these systems are not suitable for use in most surgical settings due to their size and complexity.

In the article entitled 'A system for ultrasound-guided computer-assisted orthopaedic surgery' by Chen et al, in Computer Aided Surgery, September/November 2005; 10(5/6): 281-292, a method for non-invasive localizing a bone of a patient using two-dimensional (ie B-mode) ultrasound (US) is presented. Chen's method includes the following points:
Preoperatively, a set of 2D freehand US images (e.g., a total of 2000 images) is acquired from the targeted anatomy along with their corresponding positional information on the US probe. These preoperative image data are used to construct a preoperative database that serves two main purposes:
to construct a preoperative 3D volumetric representation of the patient's anatomy that can be used for surgical planning (stage no. 1 in FIG. 2),
to form a preoperative searchable image data-base for use by the registration process.
Intraoperatively, the preoperative US volume is registered to the patient using intraoperative 2D US images.
In the OR, the surgeon takes a few live US images of the targeted anatomy while the position of the US probe is tracked in real time by the camera system. These intraoperative US images are used to find the physical position of the patient during the surgery (see the lower left image in FIG. 2).
A mutual information-based registration algorithm is employed to find the closest match to the live image in the preoperative image database (stage no. 2 in FIG. 2).
It should be borne in mind that the same images searched for in the preoperative database are also the ones used to construct the preoperative US volume of the targeted anatomy. Assuming the closest matching image is actually the live image, we can register the preoperative 3D US volume to the live US image (the lower right image in FIG. 2) and thus to the patient for surgical guidance (stage no. 3 in FIG. 2).

In other words, Chen's method involves constructing a large database of a couple thousand localized 2D ultrasound images preoperatively, and comparing each one of these images (or a reduced subset thereof) to an intra-operative localized 'live' 2D image of the bone. If there is a good match between one of the 2D images in the database and the live 2D image, it is assumed that the live image was acquired in the same plane as the localized one in the database. Therefore, a fundamental requirement of Chen's method to accurately track the bone is that there must be a 2D image in the so-called preoperative database that has been acquired in the same acquisition plane that the intra-operative US image has been acquired in, otherwise the matching algorithm cannot accurately determine the location of the bone. Another drawback is that any patient motion occurring during the pre-operative acquisition of 2000 or so images will result in relative errors between the pre-op image slices in the database (i.e. volumetric errors in the preoperative 3D US Volume).

SUMMARY

It is an object of the present invention to:
(1) Provide a non-invasive means for accurate and robust measurement and tracking of the motion of a bone using a volumetric US transducer;
(2) Provide relative measurements of one bone relative to another bone of a joint;
(3) Decompose relative joint motion into specific components; and
(4) Measure joint kinematics, instability and range of motion.

In one embodiment, a method for non-invasively tracking a bone of a subject in three-dimensional space includes the following steps:

a. Acquiring a first reference image volume I0 of a bone surface with a volumetric ultrasound imaging transducer at an initial time t0;

b. Acquiring a second image volume I1 of a bone surface with the volumetric ultrasound imaging transducer at a second time t1;

c. Measuring the three-dimensional position of the volumetric imaging transducer with a three-dimensional position measuring device at times t0 and t1 and associating each position with the corresponding image volumes I0 and I1;

d. Searching for a relative position of I0 and I1 for which the overlapping portions of the image volumes of I0 and I1 best match each other;

e. Determining the 3D transformation between the first reference volume and the second image volume that corresponds to the best-match position; and f. Repeating steps b to e

BRIEF DESCRIPTION OF THE DRAWING FIGURES

FIG. 1 is a perspective view of a bone motion tracking system according to one embodiment of the present invention;

FIG. 2c is an illustration of the ultrasound image volumes A and B in a matched position;

FIG. 4 is a perspective view of ultrasound image volumes on a femur.

DETAILED DESCRIPTION OF THE INVENTION

Figure 2A:
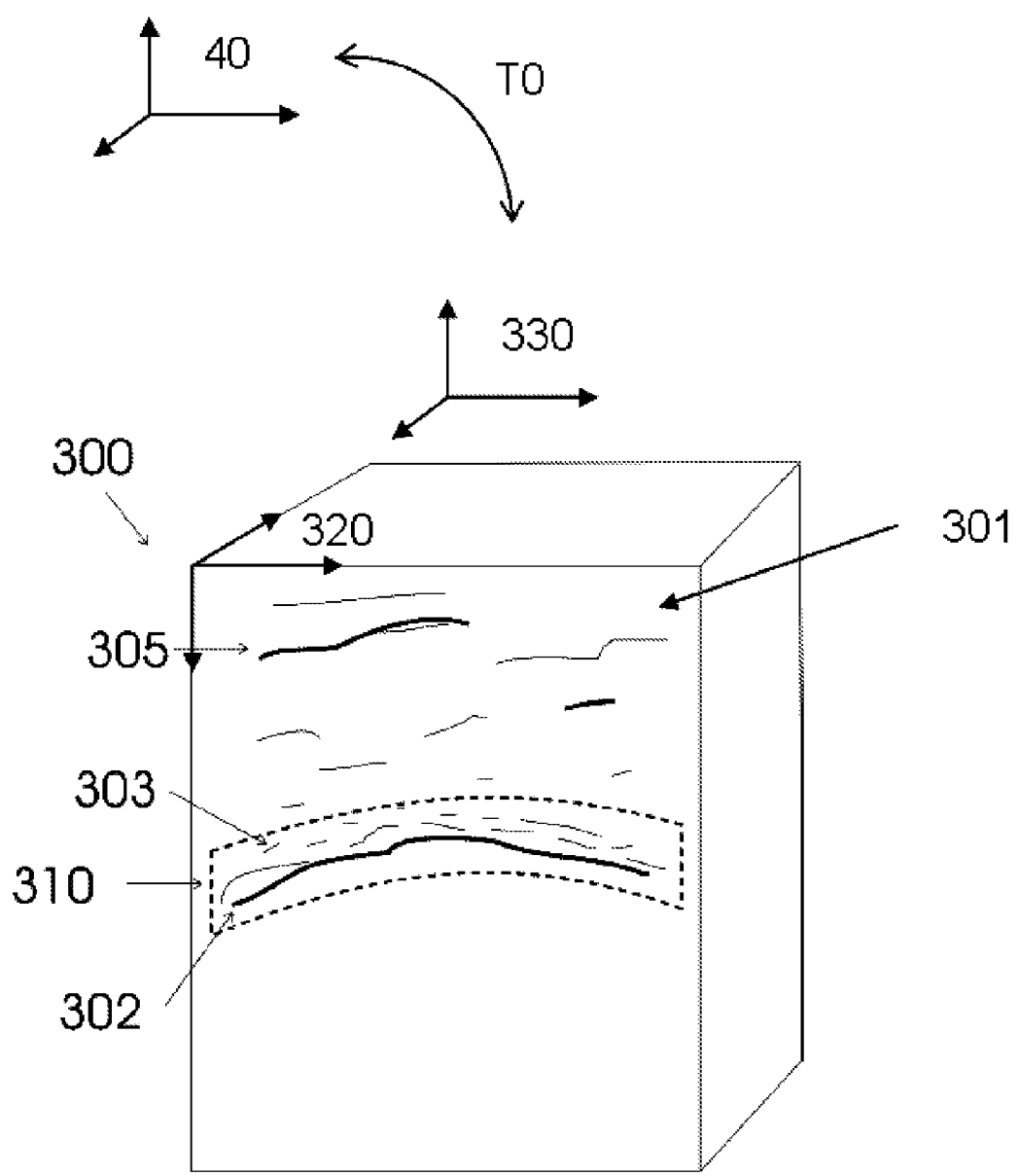
FIG. 2a is an illustration of an ultrasound image volume A.

Referring now to FIG. 1, a computerized bone motion tracking system 1 is illustrated. The system is composed primarily of at least one of each of the following elements: a three dimensional (3D) positioning measurement system 20, a computer 10, a marking element 110, and a volumetric ultrasound transducer 105.

Detecting and determining the position and orientation of an object is referred to herein as "tracking" the object. The 3D positioning measurement system 20 is capable of detecting and determining the position of marking elements 110 in a world coordinate system 40 (i.e. in 3D space). To provide precision tracking of objects, markers 10 can be rigidly connected together to form reference bodies that have an associated reference coordinate system 101, and these reference bodies are attached to the ultrasound transducer 105, digitizing point probes 120, tools, and other objects to be tracked. One such optical device that has been found to be suitable for performing the tracking function is the Polaris™ system from Northern Digital Inc., Ontario, Canada. The position measurement device 20 is described in greater detail in a number of publications, including U.S. Pat. Nos. 5,564,437 and 6,725,082, both of which were previously incorporated by reference.

The 3D positioning measurement system 20, can be any type of system known in the art, including optical, infrared, electromagnetic, radiofrequency, ultrasound based, or any other type of position measurement system. An example of a radiofrequency based tracking system can be found in United States Patent Application 2006/0250300, entitled RF system for tracking objects, which is hereby incorporated in its entirety. Another example of a position measuring systems can be found in United States Patent Application Publication number 2005/0245821, entitled Position Sensing System for Orthopedic Applications, which is hereby incorporated in its entirety.

The marking elements 110 are trackable by the 3D positioning measurement system 20. Thus the type of marking element corresponds to the type of tracking system employed, and can include passive retro-reflective markers, active, infrared, magnetic (active or passive), radiofrequency, ultrasound based, etc.

The ultrasound transducer 105 is preferably a volumetric 3D or 4D ultrasound probe that is capable of acquiring a 3D image pixel volume I04. In order to acquire 3D volumetric images the ultrasound transducer 105 can contain a 2D surface array of transducing elements. This arrangement has the advantage that a 3D volume can be acquired virtually instantaneously (i.e. in real time). In another embodiment, the ultrasound transducer 105 contains a single row of elements that acquire a 2D planar image, and are translated or rotated by mechanical means in order to build a 3D volume by acquiring a series of several image planes while registering the relative location of each plane. Volumetric 3D ultrasound probes are readily available today, such as those marketed by the companies GE (General Electric Voluson™ 730 Pro) and Philips (Live 3D Echo products, xMATRIX™ http://www.medical.philips.com/main/products/ultrasound/products/technology/live_3d.html#top). U.S. Patent Application Publication No. 20050033173 provides additional background information on multi-dimensional 3D and 4D volumetric ultrasound imaging devices. The volumetric ultrasound transducer 105 is preferably a custom built transducer that has a linear or a concave shape to better fit the patient and better image bone surfaces, which are typically convex.

Marking elements 110 are rigidly attached to the ultrasound transducer 105. Thus the position of the ultrasound transducer 105 and its imaging volume I04 can be tracked in space, or in the co-ordinate system 40 of the positioning measurement system 20. The marking elements can be attached to ultrasound transducer 105 in one of many different positions and can be locked in place before starting the bone-tracking step, for example, to optimize visibility of the marking elements with respect to the camera if an optical system is used. The marking elements could also be arranged so that they can be visible from any viewing angle, such as is described in U.S. patent application Ser. No. 11/687,324, hereby incorporated by reference in its entirety. The ultrasound transducer 105 can be attached to the subject using any number of different means, for example, with straps 107, or adhesive tape or the like. Alternatively, it could simply be held in place or pressed up to the skin by an operator or by a mechanical arm that is attached to a table that the subject is lying on.

Marking elements 110 have an associated co-ordinate system 101 which is stored in the computer 30. Thus whenever the marking elements 110 are visible and are being tracked by the positioning measurement system 20, the position of co-ordinate system 101 in the co-ordinate system 40 is known at any instant in time. Image volume I04 has an associated co-ordinate system 102. The relationship between co-ordinate system 101 and 102 is fixed and can be known. The bone 2 has a co-ordinate system 103 associated with it.

Referring now to FIG. 2a, a close up view 300 of the ultrasound image volume 300 is shown, having a 3D image coordinate system 320. Image coordinate system 320 represents the coordinate system 102 in FIG. 1, and coordinate system 330 represents the marker coordinate system 101 in FIG. 1. A single 2D image slice 301 or cross section of the 3D image volume 300 is also shown schematically in FIG. 2. The image volume 300 and slice 301 contains an image or representation 302 of the bone surface 106, as well as any overlying bone tissues such as the peilostium, muscles, ligaments, tendons, fascia and skin. The bone surface 302 is at least partially visible in the image volume. Other tissues 305 overlying the bone surface can also be seen.

Figure 3:
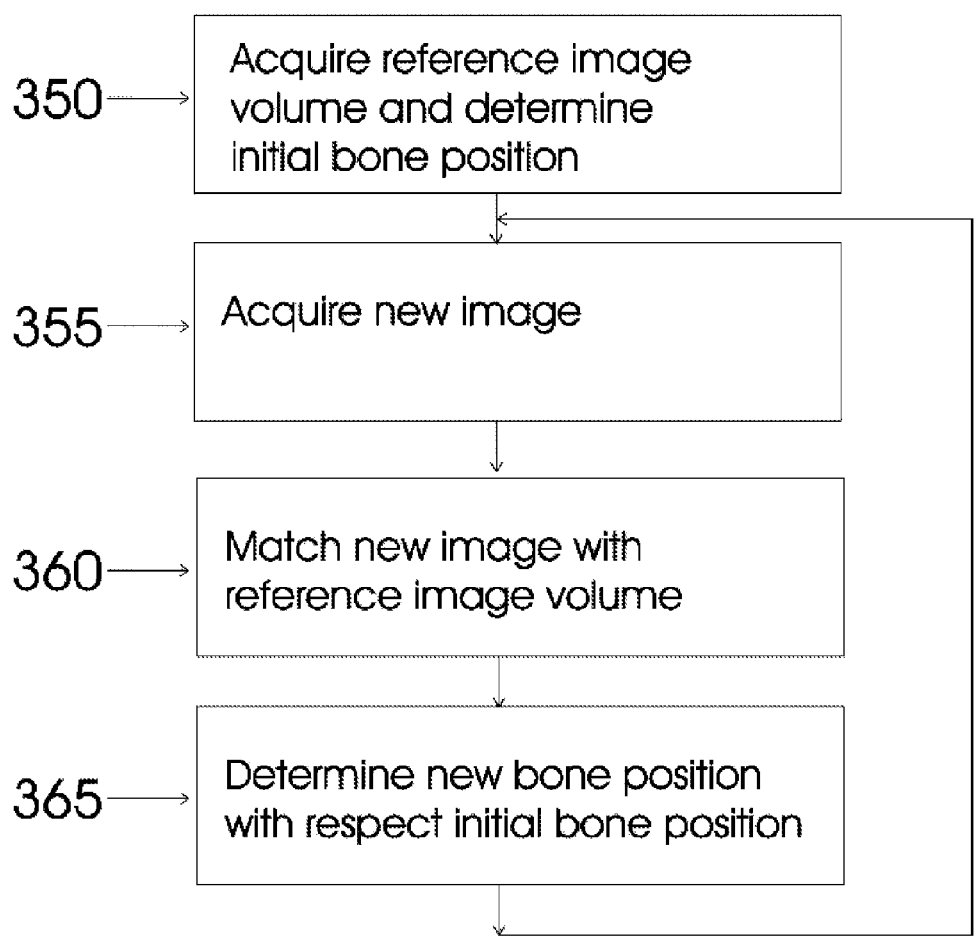
FIG. 3 is a schematic flow chart illustrating a tracking process according to the present invention.

An overview of the steps of the tracking process are shown in FIG. 3. At the beginning of the bone tracking step 350, an initial reference image volume (I0) (image 300) of 3D ultrasound image data having co-ordinate system 320 is acquired and stored in the computer 30. For explanation purposes, this reference image volume is acquired at time t0. The position of co-ordinate system 330 is also simultaneously acquired at time t0 (i.e., at the same time as the reference image volume 300) with the position measurement system 20 and stored in the computer 30 as matrix transformation T0. The transformation between the marker coordinate system 330 and the image coordinate system 320 is fixed as mentioned previously, since the markers are rigidly attached to the probe 105. Using this initial reference volume 300 and transform T0, the initial bone position is determined. At this point, an associated bone co-ordinate system 103 can be established that is linked to the marker coordinate system 330 and the image coordinate system 320 in the initial reference image volume dataset 350.

Figure 2B:
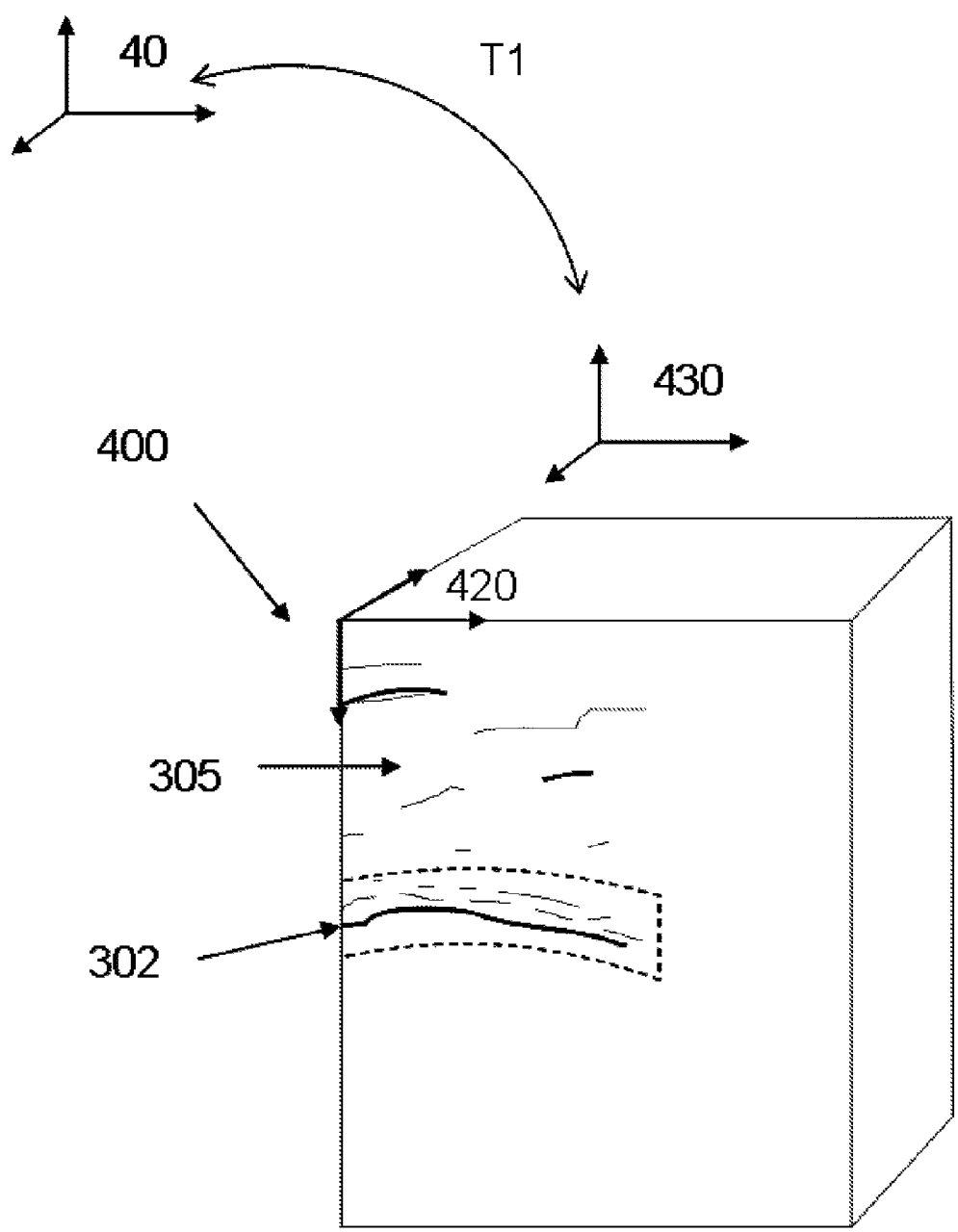
FIG. 2b is an illustration of an ultrasound image volume B.

In step 355, a second image volume 400 (I1) (see FIG. 2b) is acquired while simultaneously tracking the ultrasound transducer 105 at time t1. This new image 400 can be another complete 3D image volume whose position is measured with the position measurement system 20 and stored in computer 30 as transformation matrix T1, and therefore known in space. As can be seen in FIG. 2b, the anatomical structures (302, 305) in the new image volume 400 may be displaced in the image coordinate system 420, in comparison to the reference image coordinate system 320 due to underlying motion of the bone relative to the patients' skin and to the transducer 105.

As illustrated in FIG. 2c, the new image 400 is then matched to the initial reference image volume 300, in a 3D to 3D matching step 360. In the matching process, the new image 400 is displaced in the reference image coordinate system 320 and the overlapping areas of the two image volumes are compared to determine how well they correspond to each other in each position. A mathematical optimization process is carried out to search for the relative position Tm that best aligns (or matches) the new image with the reference image. Several techniques are known for matching image volumes to one another including intensity based techniques such as similarity measures, mutual information, correlations. The paper entitled *Mutual Information-Based Rigid and Nonrigid Registration of Ultrasound* Volumes by R. Shekhar and V. Zagrodsky, published in IEEE Transactions on Medical Imaging 21, 1 Jan. 2002, pp 9-22, teaches some methods of how to match or register two 3D image datasets with one another, and is hereby incorporated by reference in its entirety. Rigid or non-rigid matching may be performed. Many variations of the matching process are possible.

In a preferred embodiment of the present invention, only a select volume or region of interest of image is used to match the two images. Limiting the volume of pixels used in the matching process can increase the time taken to find the best match, approaching near real-time tracking performance. This region would ideally be the area 310 surrounding the rigid bone surface 302. Using the region around the bone has the advantage of avoiding inaccuracies due to poor matching because of deformations and relative movement of soft-tissues 305 such as muscles, vessels, fascia, and skin that are visible in image above the bone surface. Tissue deformations can occur when the subject is moving or walking, as in the case of gait analysis, or when the surgeon is manipulating the joint of a patient undergoing surgery.

In another embodiment of the invention, the ultrasound transducer is placed in an area in which soft tissues attach to the bone surface, such as at the site of ligament, tendon or joint capsules insertions, etc, and are visible in the image 303. It is assumed that motion of these tissues is negligible in the zone just above the bone surface. In this case, these tissues form an image texture 303 above the bone surface and are used to make the matching process more robust and accurate. In addition, if the bone surface was particularly symmetric or flat in the image volume, the overlying texture 303 in the image can help the matching algorithm converge to the correct solution and can prevent the two images from sliding on the axis or in plane of symmetry and converging to a false result. For example, if the bone shape in the reference and new images was primarily cylindrical, the matching algorithm could tend to converge at local minimum when the two cylinders are aligned but are not at the same axial position (due to the symmetrical shape of the bone). The unique texture of the tissues just above the bone surface could help to match the new image to the reference image in the correct axial location. The same advantages apply to planar and other symmetrical bone shapes.

The volume of interest 310 could be segmented out of the reference image volume just after the initial acquisition 350 and also in the new image 355 just after it is acquired. Preferably fast, real-time, and fully automatic segmentation techniques are used. Several techniques for segmentation of bone surfaces in ultrasound images have been published and are known. One example of a fully automated method for segmenting bone surfaces in ultrasound images can be found in the article *A Fully Automated Method for the Delineation of Osseous Interface in Ultrasound Images* by V. Daanen, J Tonetti, J Troccaz, in C. Barillot, D. R. Haynor, and P. Hellier (Eds.): MICCAI 2004, LNCS 3216, pp. 549-557, 2004. Springer-Verlag Berlin Heidelberg 2004, which is hereby incorporated by references in its entirety. The region 310 can be defined for example by an offset from the bone surface, or by automatic analysis of the image content and pattern around the surface.

Depending on the accuracy of the segmentation process, the matching process can use either intensity (pixel) based or surface (geometrical) based techniques. Geometrical or surfaced based techniques have the advantage of being very fast. Thus in one embodiment the bone surface in the initial reference image volume 350 is segmented onto a discrete surface or set of points and matched with the same in the new image. Combinations of the two methods could also be used to take advantage of the features from both methods.

In another embodiment the new image acquired is not a complete 3D image volume but a sparse 3D volume that is reduced to a number of slices. These slices can be orthogonal to each-other (also known as 4D US images), and the bone surface in each slice can be matched to the bone surface in the initial reference image volume 350. This also has the advantage of increased image transfer and matching speed.

Optionally, to increase the size of the initial reference image volume 350, several additional located volumes of image datasets can be acquired adjacent to one another by moving the probe over the skin surface in different directions while tracking the probe. Previously referenced U.S. Patent Application 20050033173 entitled "Extended Volume Ultrasound Data Acquisition" provides details on one method that can be used for acquiring and constructing an extended image volume, which is hereby incorporated by reference in its entirety. This increases the tracking accuracy and robustness and allows more motion of the ultrasound transducer relative to the bone during the tracking process. Preferably, the bone is moved as little as possible during this step. Overlapping images are acquired and are merged together to form one enlarged 'panoramic' reference image volume. Information in the overlapping areas can be used to match each image volume to one another, along with the position data acquired by the position measuring system for each scanned volume. As the bone may move slightly in space during the acquisitions however, the position data may not accurately represent the true relative positions of the bone surfaces imaged, and therefore, his data is best used only as an initial guess or estimate of the relative positions of the volumes. Rigid or non-rigid matching may be performed with the actual image sets to more accurately construct the enlarged image reference image volume.

Once the new image has been matched to the reference image, the amount of motion (i.e. the change in displacement and orientation) that occurred between the bone and the ultrasound transducer from t0 to t1 is now quantified by matrix transformation Tm. Thus the position of the bone can be tracked relative to the image coordinate system 102 of the ultrasound transducer 105, whose position in 3D space is tracked by the position measurement system 20. By tracking the position of the ultrasound transducer 105 with marking elements 110 in the camera reference frame 40, we can track the bone in 3D space. Tools such as point probes 120, drilling and cutting guides, etc . . . can also be tracked in space by attachment of marking elements 122. Thus these objects can be tracked relative to the bone by taking into account the relative motion of the ultrasound transducer 105 and tool 120.

To increase accuracy, more than one ultrasound transducer can be used to track a bone. For example, transducers can be arranged at the hip 510 and at the knee 520 so that the bone is localized at both ends. This way, small matching errors do not translate into large position errors in areas relatively far from the image volume 104. Each ultrasound transducers can be connected together rigidly so that only one rigid body needs to be tracked, or they can be localized individually to have greater flexibility to move around. One transducer can be placed on the medial 530 and lateral 520 side of the bone as shown in FIG. 4. They can be connected together using an adjustable arch that can adjusted and then fixed to fit the different sizes and shapes of each patient.

The invention is particularly useful when tracking bones on either side of a joint, such as the femur 2 and tibia 4 of the knee. Tracking of any bone or joint can be performed, including the hip (femur and pelvis) or shoulder (scapula and humerus) elbow, ankle, vertebrae, etc.

Particular zones on each bone can be identified that are easier to perform the imaging matching on (i.e., non-symmetrical bone surfaces and bone surfaces with tissue attachments). Such zones can include but are not limited to the femoral greater trochanter, condylar areas, posterior knee areas, tubercles such as the tibial tubercles, spine of the scapula, humoral greater trochanter, sacrum, anterior superior iliac spines, pubic tubrical, and so on.

EXAMPLE

The following paragraphs describe one example of how the present invention can be implemented.

The algorithm includes several steps and is outlined below. The first step consists of producing a coarse segmentation of the bone interface in the 3D ultrasound volume. The goal of the segmentation is to select a region of interest in an area of the image which contains information. A property of ultrasound images of bone is the presence of an acoustic shadow under the bone surface interface, and as such there is no information in this region. In other words, it is not possible to image structures behind this interface. Then, from this coarse segmentation, synthetic images containing information of localization and distance from the bone interface are constructed. Finally, registration by integrating the measure of similarity information provided by the raw images and the synthetic images is performed. In the following paragraphs, the different steps of our algorithm are set forth in more detail.

Segmentation

The principle of the method for extracting points on the interface is based on the physics of ultrasound waves. The physics of ultrasound imaging indicates that the acoustic waves in a homogeneous medium decrease according to an exponential function. This property is expressed as the following:

$$u(x) = u_0 \exp^{-\alpha x}$$

$$u(x) = u_0 \exp^{-(alpha)x}$$

In the above equation, $u_0$ is the amplitude of the wave at the entrance in the medium, x represents the distance, and α (alpha) is the absorption coefficient of the medium.

The idea for extracting the bone interfaces in the images is to try to correlate ultrasound profiles of ultrasonic beams with an exponentially decreasing function modeling the absorption of the acoustic wave in a given medium. The correlation for local maxima of each ultrasound scanline is calculated and when this correlation is higher than 90%, a bone interface is considered to exist. To speed up the process, a lower threshold to remove local minima is applied, i.e., calculate the correlation for an intensity greater than or equal to 30. This threshold is justified by the fact that the bone appears to be hyperechoic in the ultrasound images.

The average absorption coefficient of ultrasonic waves in the (cortical) bone is on the order of 3 to 10 $dB.cm^{-1}.MHz^{-1}$. The bone stops ultrasonic waves and they do not enter inside the bone so that we can calculate the correlations in the restricted depths (about 0.75 cm). This property of the bone explains the presence of the acoustic shadow behind the bone interfaces.

For the 3D ultrasound volumes, the first step to extract the bone surface is to apply the method described above on each scarline of the ultrasound volume. The detection of the interface is not perfect because there is a lot of noise and ultrasound images can be of relative low quality and there are outliers and "holes" in the surface. A few steps are added therefore to "clean up" the surface. First, any isolated and small clusters of points are removed. The number of neighbor points (3×3×3 neighborhood) around the considered point are counted. Then, the point is kept only if the number of its neighbors is greater than or equal to (3×3−1)/2. We iterate until stability. To fill in the "holes", a morphological dilatation is made by a sphere with a radius of 1 (to avoid the displacement of the interface while it is being thinned). Plane by plane is skeletonized to smooth and thin out the point cloud. Finally, a "bone morphing" step is performed in which a surface is deformed to the cloud of points. At the end of the "bone morphing" step, we remove the outliers which are more than 1 mm from the surface are removed. Finally, a second "bone morphing" step on the cleaned-up cloud of points is performed.

Panoramic Volume

Next, a panoramic ultrasound reference volume is built. Accurate registration of 3D or 4D ultrasound images (images that may contain little information) to a reference volume requires a maximum of overlap. It is thus advantageous to have a large reference volume.

The invention uses a 3D ultrasound/3D ultrasound voxel based registration method to match ultrasound volumes. The volumes can be located in the world co-ordinate frame of the camera or with respect to a reference body attached non-invasively to the skin of the patient (i.e. an external marker attached to the patient non-invasively with straps or adhesive tape). Because the patient may move during the acquisition or because the reference marker is not rigidly fixed to the structure to track, it is necessary to compensate for this movement during the acquisitions of the panoramic volume. This method of registration allows one to build panoramic volumes to compensate for the small size of the original volumes and maximize the overlap between the 4D images and the reference volume for the dynamic tracking (i.e. the next step)

The particularity of the present registration method is to combine the information given by the intensities contained in the image and the information given by a coarse segmentation of our images.

The first stage of the registration algorithm is to produce a coarse segmentation of the bone interface using the method that was explained previously. This segmentation can define different regions in the image: regions corresponding to the bone interface, regions ahead of interface, regions behind the interface and regions with no specific information. Starting from the distinction between these different regions, a concept of distance to the interface has been added which enables the building of an image containing this information. This image is constructed as follows: the bone interface (obtained by the segmentation) is modelized by a Gaussian, for the regions located in front of and behind the interface a linear model is used. This linear model represents the distance to the interface. The others regions are not considered.

To register the images, a voxel-based registration method is used. The normalized cross-correlation is used. The optimization procedure is the Powell-Brent algorithm. The similarity measure is modified to integrate the information containing in the synthetic images. A multiplicative factor (pixel to pixel) is calculated which penalizes the similarity measure calculated on the raw image. This factor is a kind of normalized SSD (sum of the square differences) calculated pixel-to-pixel on the images.

Bone Tracking

The bone tracking step requires a <<real time>>3D/3D or 3D/4D ultrasound registration algorithm (i.e. to constantly register new images to the reference volume). The 3D/3D registration algorithm described previously for building a panoramic volume can be naturally extended for tracking. This algorithm can be optimized to match (or register) the bone in order to track it in real-time, using a multi-resolution approach, and/or by performing calculations on a graphics board (video card) to speed up the process and computation time. As mentioned previously, the algorithm can register either a 3D volume obtained in "real time" (for example, with a matrix probe) or two orthogonal ultrasound slices obtained in "real time" (for example, with a mechanical probe) to the reference volume. The initial attitude (i.e. the transformation used as the initial 'guess' of the best-match search algorithm) used for the registration at the instant $t_{i+1}$ can be given by the previous registration at the instant $t_i$ and should be close to the best 'matched' solution. Consequently, the size of the research space is reduced and thus the registration process is faster.

In one embodiment of the present invention, the non-invasive bone tracking system is used to measure relative motion of at least two bones of a joint, in which one bone is tracked with the non-invasive ultrasonic method, and the other bone is tracked by simply attaching the marking elements 112 to the skin with straps 112 or plates. A cast could also be used to fix the second tracker to the patient, such as on the tibia or arm. To measure shoulder motion and stability, a cast can be put around the for-arm and biceps to fix the elbow at a particular flexion angle, such as at 90 degrees. Scapular motion can then be measured by strapping the tracked ultrasound transducer to the spine of the scapula or near the neck of the gleniod on the posterior side.

Some examples of use of the system are as follows: knee stability testing to diagnose an injury or to compare pre and post operative kinematics. Tests such as the Anterior posterior drawer test, lauchman test, pivot shift test, varus valgus stress test could be quantified non-invasively. U.S. Patent Application Publication No. 20060161052 entitled "Computer assisted orthopaedic surgery system for ligament graft reconstruction describes methods for calculating the abovementioned parameters, and for decomposing relative joint motion into specific components", which is hereby incorporated by reference in its entirety. Hip range of motion could also measured pre and post-operatively, and gait analysis can be performed eliminating the errors due to skin motion. Shoulder range of motion, stability, scapular kinematics can be quantified. The system is also adapted for surgical use such as orthopaedic procedures.

It will be appreciated by persons skilled in the art that the present invention is not limited to the embodiments described thus far with reference to the accompanying drawings; rather the present invention is limited only by the following claims.

What is claimed is:

1. A method for non-invasively tracking a bone of a subject in three-dimensional space, the method comprising:
    (a) attaching a 3D or 4D volumetric ultrasound imaging transducer to the subject and acquiring a first reference image volume I0 of a bone surface with the 3D or 4D volumetric ultrasound imaging transducer at an initial time t0, wherein the 3D or 4D volumetric ultrasound imaging transducer acquires 3D image pixel volumes;
    (b) determining an initial position of the bone using the first reference image volume I0;
    (c) acquiring a second image volume I1 of the bone surface with the 3D or 4D volumetric ultrasound imaging transducer at a second time t1;
    (d) measuring a three-dimensional position of the 3D or 4D volumetric ultrasound imaging transducer with a three-dimensional position measuring device at the times t0 and t1 and associating each position with the corresponding image volumes I0 and I1;
    (e) searching for a relative position of I0 and I1 for which overlapping portions of the image volumes of I0 and I1 are closest aligned to one another and defining this position as a best-match position;
    (f) determining a 3D transformation between the first reference image volume and the second image volume that corresponds to the best-match position; and
    (g) repeating steps c to f.

2. The method of claim 1, wherein the best-match search is limited to a region of interest that includes pixels representing the bone surface in at least one of the first reference image volume and the second image volume.

3. The method of claim 2, whereon the region of interest includes the bone surface and a finite region of soft-tissues overlying the bone surface.

4. The method of claim 1, wherein the second image volume is a sparse 3D volume.

5. The method of claim 4, wherein the sparse 3D volume is limited to two or three orthogonal image planes.

6. The method of claim 1, wherein the determined 3D transformation is used as an initial guess for a first relative position used in the best-match search of step (e) for a next successive tracking step.

7. The method of claim 1, wherein the first reference image volume is an extended panoramic volume made up of several image volumes acquired adjacent to one another and matched with one another.

8. The method of claim 1, wherein the bone to be tracked is one of a femur, tibia, scapula, humerus, pelvis, scaphoid and vertebra.

9. The method of claim 1, wherein the bone to be tracked is a femur bone of a knee joint, and a marking element is non-invasively attached to a tibia.

10. The method of claim 9, wherein relative motions of the bones of the knee joint are measured and decomposed into different directions and axes of rotation.

11. The method of claim 1, wherein the bone to be tracked is a scapula bone of a shoulder joint, and a marking element is non-invasively attached to a humerus.

12. The method of claim 11, wherein relative motions of the bones of the shoulder joint are measured and decomposed in to different directions and axes of rotation.

13. The method of claim 1, wherein multiple 3D or 4D volumetric transducers are positioned at different locations to track the bone.

14. The method of claim 13, wherein the multiple 3D or 4D volumetric transducers are rigidly connected to one another and tracked by a marking element.

15. The method of claim 1, further including the step of displaying the tracked bone on a display and showing movement thereof in approximately real-time.

16. The method of claim 1, further comprising the step of increasing a size of the first reference image volume I0 by acquiring additional located volumes adjacent to one another by moving the 3D or 4D volumetric ultrasound imaging transducer over a skin surface of the bone surface in a plurality of directions.

17. A method for non-invasively tracking a bone of a subject in three-dimensional space, the method comprising:
    attaching a 3D or 4D volumetric ultrasound imaging transducer to the subject and acquiring a first reference image volume I0 of a bone surface with the 3D or 4D volumetric ultrasound imaging transducer at an initial time t0, wherein the 3D or 4D volumetric ultrasound imaging transducer acquires 3D image pixel volumes, and wherein the first reference image volume I0 has a first coordinate system;
    determining an initial position of the bone using the first reference image volume I0;
    acquiring a second image volume I1 of the bone surface with the 3D or 4D volumetric ultrasound imaging transducer at a second time t1;
    measuring a three-dimensional position of the 3D or 4D volumetric ultrasound imaging transducer with a three-dimensional position measuring device at the times t0 and t1 and associating each position with the corresponding image volumes I0 and I1;
    searching for a relative position of I0 and I1 for which overlapping portions of the image volumes of I0 and I1 are closest aligned to one another and defining this position as a best-match position; and
    determining a 3D transformation between the first reference image volume and the second image volume that corresponds to the best-match position, wherein the second image volume I1 is displaced from the first coordinate system in the best-match position.

18. The method of claim 17, wherein the best-match search is limited to a region of interest that includes pixels representing the bone surface in at least one of the first reference image volume and the second image volume.

19. The method of claim 17, wherein the second image volume is a sparse 3D volume.

20. The method of claim 19, wherein the sparse 3D volume is limited to two or three orthogonal image planes.

21. A method for non-invasively tracking a bone of a subject in three-dimensional space, the method comprising:
    (a) acquiring a position coordinate system at initial time t0 using a three-dimensional position measuring device;
    (b) attaching a 3D or 4D volumetric ultrasound imaging transducer to the subject and acquiring a first reference image volume I0 of the bone and tissue adjacent to and attached to the bone with the 3D or 4D volumetric ultrasound imaging transducer at initial time t0 while simultaneously tracking the 3D or 4D volumetric ultrasound imaging transducer;
    (c) determining an initial position of the bone using the first reference image volume I0 and the position coordinate system;
    (d) acquiring a second image volume I1 of the bone with the 3D or 4D volumetric ultrasound imaging transducer at a second time t1 while simultaneously tracking the 3D or 4D volumetric ultrasound imaging transducer;
    (e) selecting a region of interest corresponding to a subset of the first reference image volume I0 and the second image volume I1;
    (f) searching for a relative position of I0 and I1 for the selected region of interest for which overlapping portions of the image volumes of I0 and I1 are closest aligned to one another and defining this position as a best-match position;
    (g) determining a 3D transformation between the first reference image volume and the second image volume that corresponds to the best-match position; and
    (h) repeating steps (d) to (g).

* * * * *